US008481290B2

(12) United States Patent
Kongtawelert et al.

(10) Patent No.: US 8,481,290 B2
(45) Date of Patent: Jul. 9, 2013

(54) ANTIBODY SPECIFIC FOR A CHONDROITIN SULPHATE EPITOPE

(75) Inventors: Prachya Kongtawelert, Chiang Mai (TH); Tim Hardingham, Manchester (GB); Siriwan Ong-Chai, Chiang-Mai (TH); Kazuyuki Sugahara, Sapporo (JP); Peraphan Pothacharoen, Chiang-Mai (TH); Nattachai Tiengburanathum, Chiang-Mai (TH)

(73) Assignees: The National Research Council of Thailand, Bangkok (TH); The Thailand Research Fund, Bangkok (TH); Chiang Mai University of Thailand, Chiang Mai1 (TH)

( * ) Notice: Subject to any disclaimer, the term of this patent is extended or adjusted under 35 U.S.C. 154(b) by 21 days.

(21) Appl. No.: 11/628,432

(22) PCT Filed: Jun. 1, 2005

(86) PCT No.: PCT/GB2005/050077
§ 371 (c)(1),
(2), (4) Date: Jun. 4, 2007

(87) PCT Pub. No.: WO2005/118645
PCT Pub. Date: Dec. 15, 2005

(65) Prior Publication Data
US 2008/0038270 A1    Feb. 14, 2008

(30) Foreign Application Priority Data

Jun. 3, 2004  (TH) ........................................ 091280
Aug. 18, 2004 (GB) ................................... 0418415.6

(51) Int. Cl.
    C12P 21/04    (2006.01)
(52) U.S. Cl.
    USPC ..................... 435/70.2; 435/70.21; 435/70.3
(58) Field of Classification Search
    None
    See application file for complete search history.

(56) References Cited

U.S. PATENT DOCUMENTS 6,960,562 B2 * 11/2005 Jay ..................................... 514/8
2009/0202517 A1    8/2009 Yoneyama

OTHER PUBLICATIONS

Ong-chai, Siriwan. An investigation of serum chondroitin Sulphate Epitopes for susing as markers of Osteoarthritis, Abstract PDF4380046, Jul. 2000.*
Ppthacharoen, Peraphan. The Wuantitative analysis of Chondroitin sulfate Epitopes and Hyaluronan as diagnostic markers for degenerative joint diseases by ELISA technique. Thesis Abstract, p. iv-v. 2000. http://archive.lib.cmu.ac.th/full/T/2000/bioch1000pp_abs.pdf.*
Tiengburanatam, Nathachai. Production and Characterization of Monoclonal Antibody Against Chondroitin 6-sulfate. Master of science Thesis abstract, 1996. http://archive.lib.cmu.ac.th/full/T/1996/bioch1196nt_abs.pdf.*
Owens RJ, Young RJ. The genetic engineering of monoclonal antibodies. J Immunol Methods. 168(2):149-165, 1994.*
Chiang Mai University. Chapter II, http://archive.lib.cmu.ac.th/full/T/1996/bioch1196nt_ch2.pdf. pp. 19-26, 1996.*
Chiang Mai University. Chapter II,http://archive.lib.cmu.ac.th/full/T/2003/chem1003kp_ch2.pdf. pp. 27-53, 2003.*
Bost KL, Pascual DW. Antibodies against a peptide sequence within the HIV envelope protein crossreacts with human interleukin-2. Immunol Invest. 17(6-7):577-86, 1988.*
Ito et al., "Structural characterization of the epitopes of the monoclonal antibodies 473HD, CS-56, and MO-225 specific for chondroitin sulfate D-type using the oligosaccharide library," Glycobiology 15(6): 594 (2005).
Couchman et al., "Mapping by monoclonal antibody detection of glycosaminoglycans in connective tissues," Nature 307: 650-52 (1984).
Ito et al., "Structural characterization of the epitopes of the monoclonal antibodies 473HD, CS-56, and MO-225 specific for chondroitin sulfate D-type using the oligosaccharide library," Glycobiology, Dec. 29, 2004, 15(6): 593-603.
Tiengburanatam, "Production and Characterization of Monoclonal Antibody Against Chondroitin 6-Sulfate," M.S. Biochemistry Thesis, Chiang Mai University, Nov. 1996.
John T. Gallagher & Andrew Walker, Molecular Distinctions Between Heparan Sulphate and Heparin, 230 Biochemistry Journal 665-674 (1985).
Julia I. Ellyard et al., Eotaxin Selectively Binds Heparin: An Interaction that Protects Eotaxin from Proteolysis and Potentiates Chemotactic Activity in Vivo, 282 Journal of Biological Chemistry 15238-15247 (2007).

* cited by examiner

*Primary Examiner* — Maher Haddad
(74) *Attorney, Agent, or Firm* — McDonnell Boehnen Hulbert & Berghoff LLP

(57) ABSTRACT

An antibody specific for a chondroitin sulphate epitope is described, as is a hybridoma cell line which produces such an antibody. The antibody is useful in the diagnosis and treatment of connective tissue diseases, such as arthritis and sarcomas. Test kits and pharmaceutical compositions are also described.

1 Claim, 9 Drawing Sheets

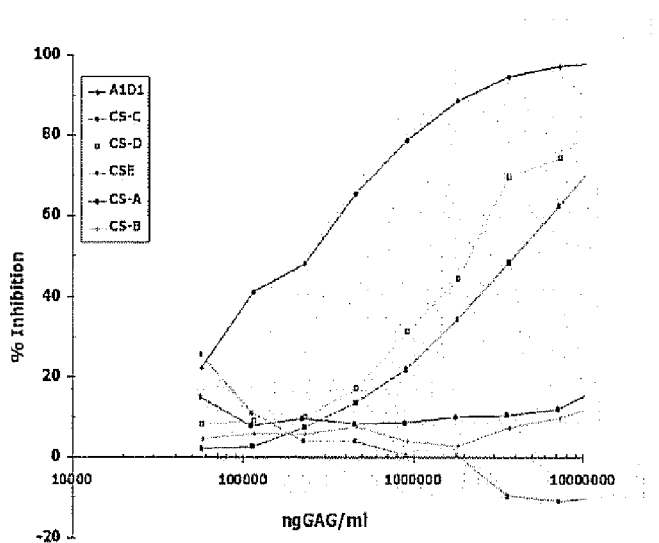
Figure 1 Graph showing the characteristics of monoclonal antibody WF6 reacting with various chondroitin sulfates
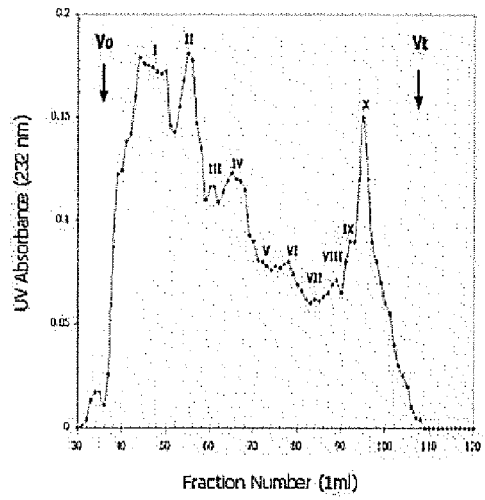
Figure 2 The column profile of oligosaccharides containing chondroitin 6-sulfate from chondroitinase ABC digested CS-C on BioGel P-6 gel filtration

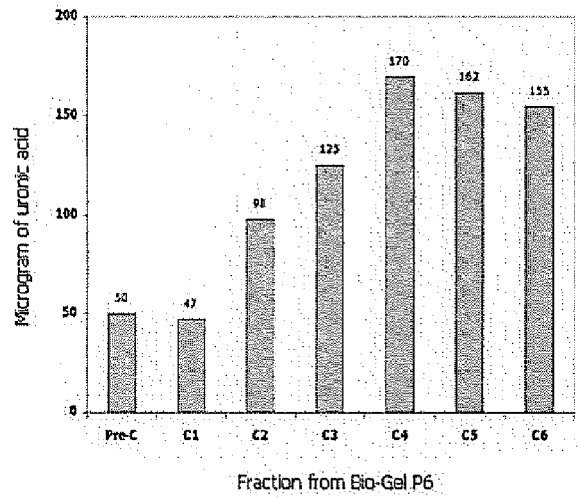

Figure 3. The level of uronic acid in each fraction of oligosaccharides from BioGel P-6 column chromatography which gives reactivities against MAb WF6 at 50 % inhibition (IC50) using competitive ELISA. The number shown in the graph is the amount of uronic acid in microgram.

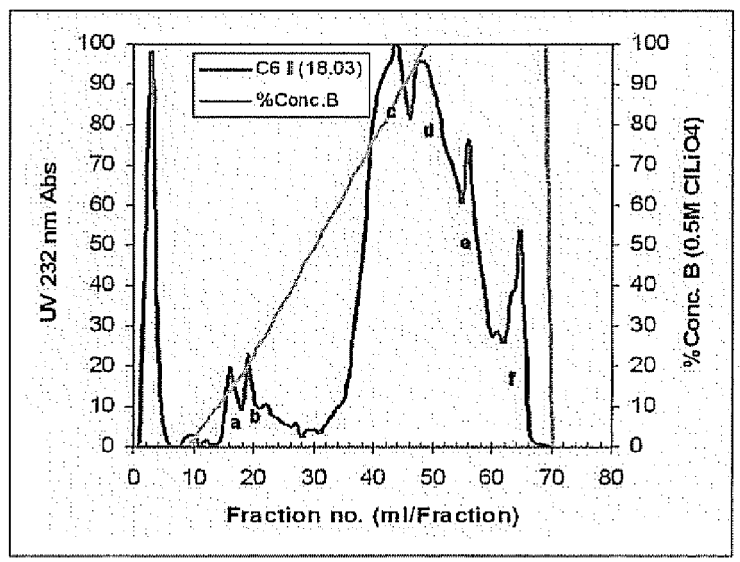

Figure 4 Graph demonstrating the column profile of fraction 6 (from BioGel P-6) on Mono-Q ion-exchange FPLC

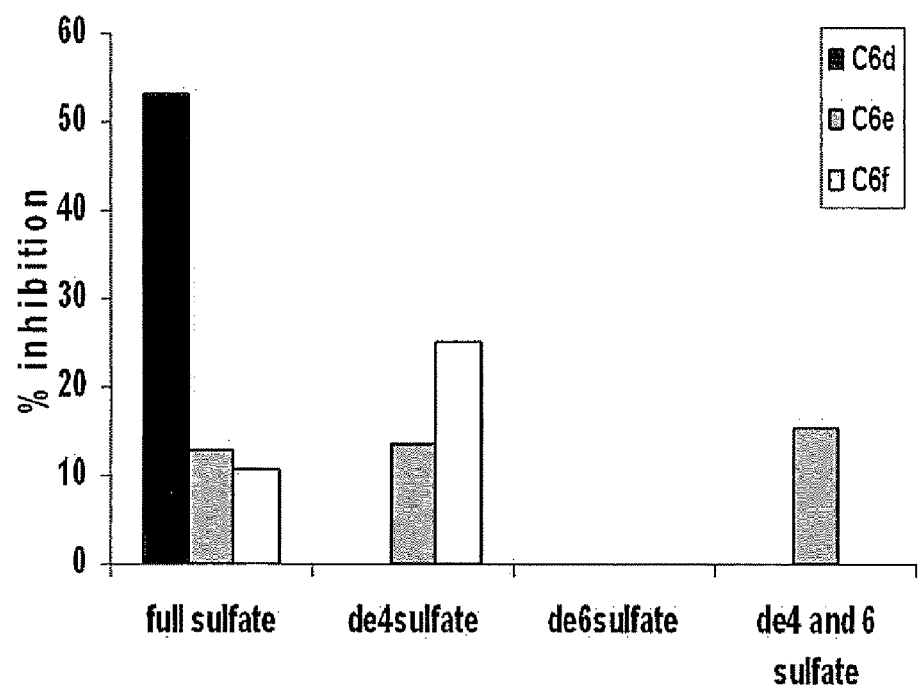
Figure 5 Graph demonstrating the effect of sulfatase enzyme on the reactivities of oligosaccharides digested with 4- and 6-sulfatase against MAb WF6

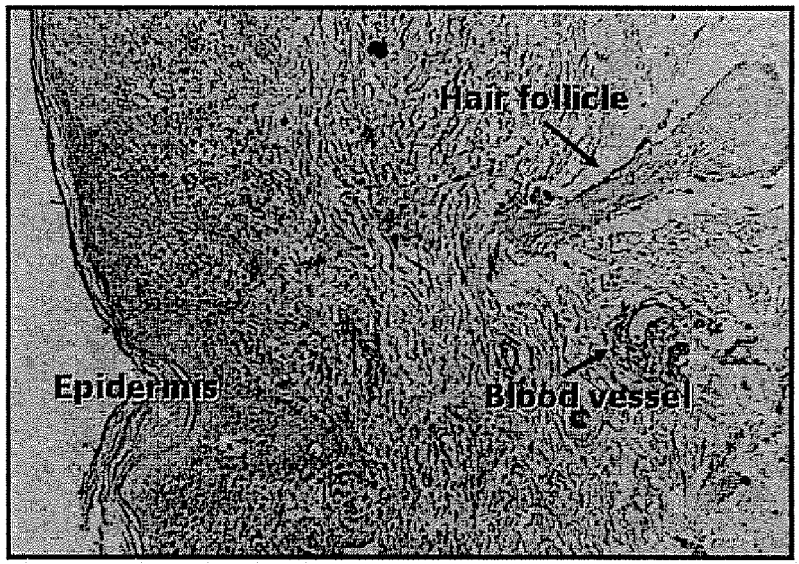
Figure 6. The immunohistostaining of human skin tissue section with MAb WF6 as primary antibody.
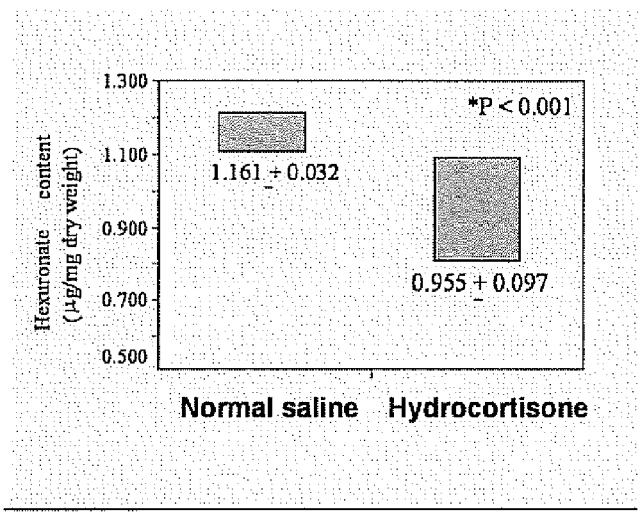
Figure 7 The proteoglycan content (as uronic acid) in cartilage from the animal treated with intra-articular injection of normal saline solution and hydrocortisone

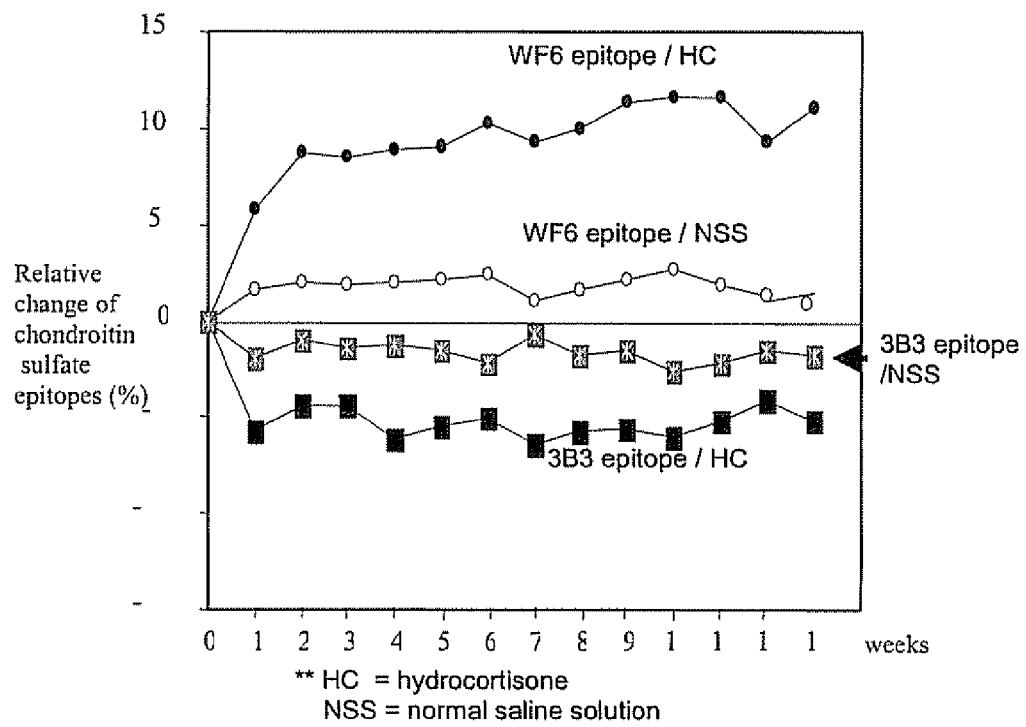
Figure 8 The level of WF6 epitope as catabolic marker and 3B3 epitope (anabolic marker) in the animals treated with normal saline solution and hydrocortisone group

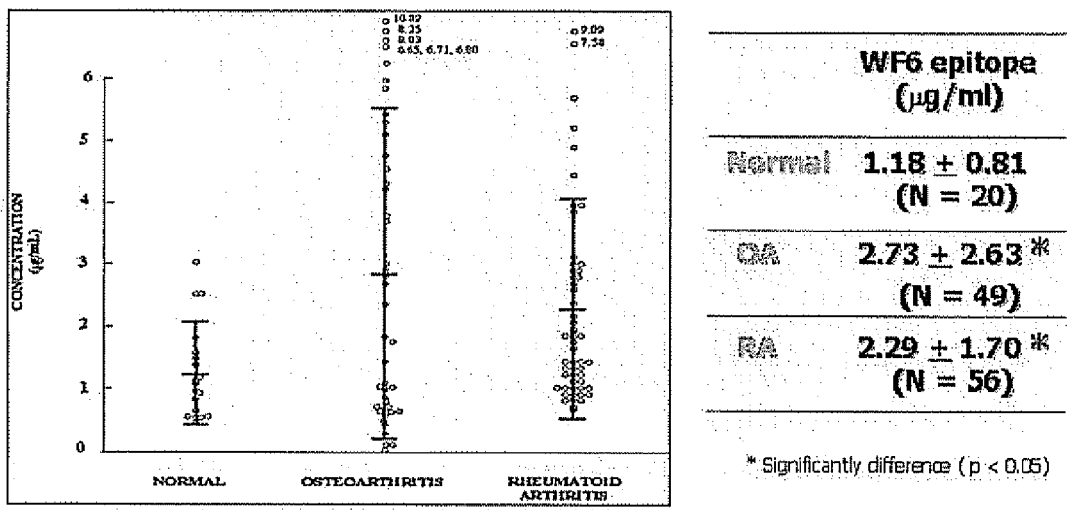
Figure 9 A scatter graph showing the level of WF6 epitope in serum of normal (N = 20), OA (N = 49) and RA (N= 56), the significant level is p < 0.05 using student t-test.

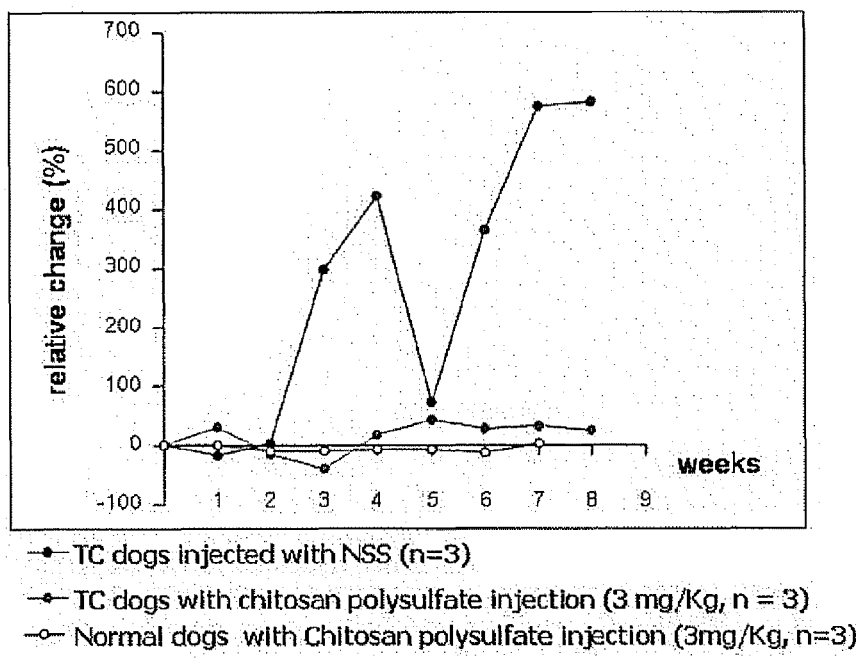
Figure 10. Comparison of the effect of chitosan polysulfate on the level of WF6 epitope and normal saline solution in the cruciate ligament transection in dog model. The relative change is determined by percentage of the level against the pre-treated period (week 0).

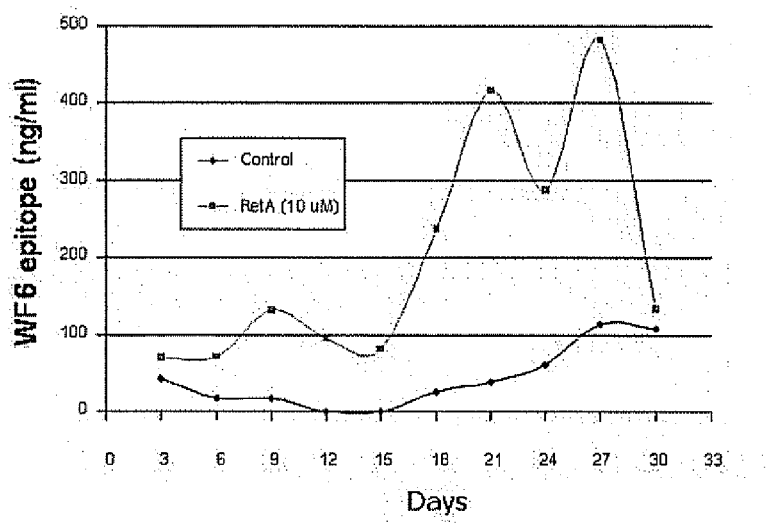
Figure 11 The level of WF6 epitope in cartilage explants culture which have been quantitated by competitive ELISA using monoclonal antibody WF6 for the monitoring the degradation by retinoic acid induction

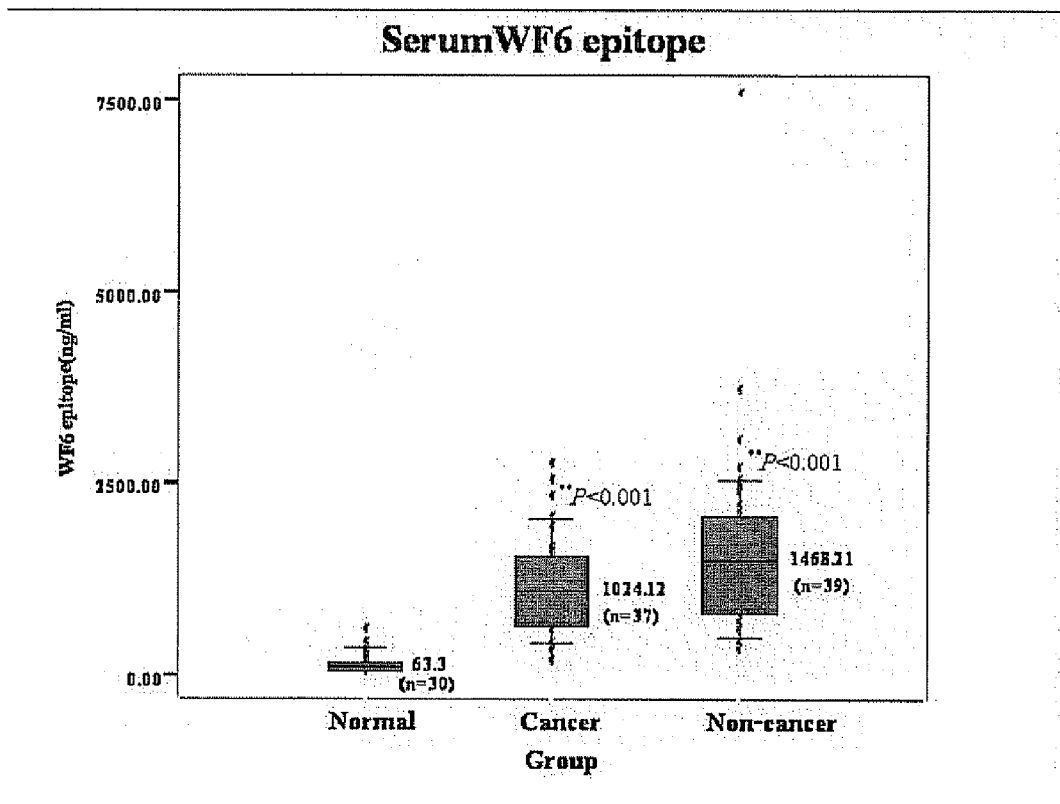
Figure 12. The level of proteoglycan containing chondroitin 6-sulfate WF6 epitope in serum from normal, ovarian cancer group and ovarian non-cancer (tumour). The significantly difference between group shown as $p < 0.05$ by student t-test.

ANTIBODY SPECIFIC FOR A CHONDROITIN SULPHATE EPITOPE

FIELD OF THE INVENTION

The present invention relates to an antibody and to methods for producing the antibody. Aspects of the invention also relate to diagnostic methods, test kits, and pharmaceutical compositions using the antibody. More particularly, the antibody of the present invention is an antibody to chondroitin sulfate.

BACKGROUND TO THE INVENTION

Joint diseases resulting from osteoarthritis and other diseases which trigger the destruction of cartilage are causes of economic and social loss, and can be considered as major health problems (1, 2).

Osteoarthritis results from the degradation of articular cartilage. It is estimated that up to 60% of the population aged over 75 years old suffer from this disease (3). The real cause of osteoarthritis is still unknown but some reports mention that while this disease is developing cartilage, subchondral bone and synovial membrane undergo some changes. The pathogenesis of this disease causes the affected cartilage to lose resistance to outer impact and also the elasticity and smoothness of the joint.

While rheumatoid arthritis is a progressive destruction of the cartilage similar to osteoarthritis (OA), patients suffering from rheumatoid arthritis (RA) experience the tearing and destruction of macromolecules which are major components of cartilage by proteolytic cleavage; the degradation products are then released to the synovial fluid. The degradation of the surface of articular cartilage and cartilage thickness can be assessed by x-ray diagnosis of the affected joints, but this will only be apparent after a long period of these diseases, which can often be too late for treatment (4, 5).

Provision of an alternative diagnostic test for arthritis and/or other cartilage degradation would therefore be beneficial to patients. In particular, detection of cartilage degradation products in synovial fluid would assist in the development of diagnostic tests which allow diagnosis at an early stage. Such a test may also assist in monitoring the disease and as a prognosis marker at the different stage of the diseases.

There is an existing test for diagnosis of degenerative joint diseases (6). Quantitation of proteoglycans and their fragments, especially glycosaminoglycans, can be done by an immunoassay using specific monoclonal antibodies to the proteoglycan fragments and other biochemical markers in the cartilage. Monoclonal antibodies have been produced against proteoglycan fragments such as anti-keratan sulfate peptides (KS-peptides) (7), chondroitin sulfate epitopes (CS-epitope) (8, 9), and hyaluronan (HA) (10). Using these antibodies and binding proteins in immunoassays, especially, ELISA-based techniques, can allow a quantitative test of these biomolecules to be performed.

Furthermore, certain types of cancer are known to overproduce these and related biomolecules. Furthermore, cancers can produce many enzymes that degrade biomolecules in connective tissues surrounding them. So, proteoglycans containing chondroitin sulfate can be a useful marker indicating the existence of cancers and can be a potential marker for a prognosis or treatment of disease activities.

SUMMARY OF THE INVENTION

The present inventors have created a hybridoma cell line which produces a monoclonal antibody specific for a particular chondroitin sulfate epitope. The antibody is designated WF6, and the cell line has been deposited under the Budapest Treaty with the American Type Culture Collection (ATCC) having an address of 10801 University Boulevard, Manassas, Va. 20110-2209, under accession number PTA-6157, and having a date of receipt of Aug. 11, 2004. The cell line will be referred to herein as "the WF6 cell line", while "WF6" alone will refer to the antibody. The antibody is shown herein to specifically recognise a short oligosaccharide epitope comprising chondroitin sulfate, and in particular an epitope including at least one chondroitin 6-sulfate unit. A chondroitin sulfate chain consists of a repeating disaccharide unit, D-glucuronate and N-acetyl-D-galactosamine-sulfate linked in a β 1-3 linkage; the chondroitin sulfate oligosaccharide comprises multiple chondroitin sulfate units. Chondroitin sulfate is found in a number of forms, the main ones of which are chondroitin 4-sulfate (also referred to as chondroitin sulfate A, CSA), chondroitin 6-sulfate (or chondroitin sulfate C, CSC), and chondroitin sulfate D, CSD.

According to a first aspect of the present invention, there is provided a WF6 antibody produced by cell line WF6, or an antibody having equivalent specificity to the WF6 antibody.

The invention also comprises functional derivatives of such an antibody, which show the same specificity. Functional derivatives include Fab, Fab' and F(ab)$_2$ fragments; single chain antibodies; and functional fragments obtained by chemical or enzymatic cleavage of the antibody or molecular biological methods such as phage display technique. Chimeric antibodies are also included within the scope of the invention. The invention further comprises labelled antibodies and functional derivatives thereof. Labelled antibodies include enzyme conjugated antibodies, biotinylated antibodies, fluorescently and radioactive labelled antibodies, gold labelled antibodies, and such like. The skilled person will be aware of suitable techniques for preparing such derivatives; confirming that the antibody has the required specificity may be achieved using the techniques detailed herein which were used to determine the WF6 antibody specificity.

According to a further aspect of the invention, there is provided a hybridoma cell as deposited with the American Type Culture Collection (ATCC) on 11 Aug. 2004, under accession number PTA-6157. The invention also relates to functional derivatives of such cells; that is, derived cells which also produce or are capable of producing antibodies having the same specificity as the WF6 antibody. The invention also provides an antibody produced by said cell, and functional derivatives of such antibodies.

A further aspect of the invention provides a monoclonal antibody which recognises a chondroitin sulfate oligosaccharide epitope comprising 8 sugar monomers, the epitope including at least one chondroitin 6-sulfate unit. Preferably the chondroitin 6-sulfate unit is the terminal unit. Detection of the epitope is abolished by digestion of the oligosaccharide with 6-sulfatase, and also by digestion with 4-sulfatase. The epitope is also therefore believed to comprise at least one chondroitin 4-sulfate unit. We believe that at least the sequence ΔDCCC is detected by the WF6 antibody; other specific sequences may also be detected.

According to a further aspect of the invention, there is provided a method of producing monoclonal antibodies, comprising culturing hybridoma cells as deposited with the American Type Culture Collection (ATCC) on 11 Aug. 2004, under accession number PTA-6157 in a suitable growth medium, or hybridoma cells producing an antibody having equivalent specificity to the WF6 antibody; and harvesting growth supernatant to obtain antibodies.

A further method of producing monoclonal antibodies, in accordance with the invention, comprises injecting hybridoma cells as deposited with the American Type Culture Collection (ATCC) on 11 Aug. 2004, under accession number PTA-6157, or hybridoma cells producing an antibody having equivalent specificity to the WF6 antibody, into the peritoneum of a host mammal; allowing a tumour to develop; and extracting ascitic fluid from the host mammal. The method may further comprise the step of priming the host mammal prior to injection to produce antibodies; for example, by pristane injection. The host mammal is preferably a non-human mammal, more preferably a rodent, and most preferably a mouse. The host mammal is also preferably of the same type, and optionally also of the same immunological background, as one of the cells used to create the hybridoma. For example, when the cell line X63 Ag 8.653 is used to create the hybridoma (as is the case for the WF6 cell line), the host mammal is preferably a Balb/c mouse.

The invention further provides a method of producing monoclonal antibodies, comprising extracting ascitic fluid from a host mammal having a tumour derived from hybridoma cells as deposited with the American Type Culture Collection (ATCC) on 11 Aug. 2004, under accession number PTA-6157, or hybridoma cells producing an antibody having equivalent specificity to the WF6 antibody.

A further aspect of the present invention relates to a method of diagnosis of diseases of connective tissue, the method comprising the steps of obtaining a sample from a patient; contacting the sample with WF6 antibody produced by cell line WF6, or an antibody having equivalent specificity thereto, or a functional derivative thereof and detecting binding of the antibody to the sample. The antibody will allow detection of degradation products of cartilage or other connective tissue which includes fragments having a chondroitin 6-sulfate component.

The sample may be taken from synovial fluid, other cellular fluid, serum, sputum, tissue samples, tissue culture media, cartilage or the like.

The step of contacting the sample with the antibody may take place in vivo or in vitro or in situ.

The detection step may comprise any convenient detection means; for example, ELISA, indirect ELISA, competitive ELISA, sandwich ELISA, radioimmunoassay, fluorescent immunoassay, chemiluminescence immunoassay, immunoblotting, immunohistostaining, immunochromatography, immunodiffusion, flow injection analysis, confocal microscope and the lice.

The detection step may further comprise quantitating the levels of antibody binding in the sample; this can allow a prognosis of the disease to be obtained.

The disease of connective tissue may be selected from the group comprising osteoarthritis, rheumatoid arthritis, cancers of the connective tissue including sarcomas, cervical and ovarian cancer, and cancer of tissues which produce chondroitin sulfate-containing proteoglycans.

The present invention also provides the use of a WF6 antibody produced by cell line WF6, or an antibody having equivalent specificity thereto, or a functional derivative thereof, in the preparation of a medicament for use in the diagnosis of a disease of the connective tissue.

A further aspect of the present invention comprises a method for diagnosing diseases of connective tissue, the method comprising detecting the presence of chondroitin sulfate oligosaccharides comprising at least 8 sugar monomers, at least one of which is chondroitin 6-sulfate, in a sample. The detection is preferably carried out using a WF6 antibody or an antibody having equivalent specificity thereto.

The present invention further provides a method of detecting chondroitin sulfate oligosaccharides comprising at least 8 sugar monomers, at least one of which is chondroitin 6-sulfate, in a sample, the method comprising contacting the sample with WF6 antibody produced by cell line WF6, or an antibody having equivalent specificity thereto, or a functional derivative thereof; and detecting binding of the antibody to the sample.

A further aspect of the invention provides a test kit comprising a WF6 antibody produced by cell line WF6, or an antibody having equivalent specificity thereto, or a functional derivative thereof. The skilled person will be aware of suitable protocols for the detection of binding of the antibody to a target; for example, various protocols are described herein. The kit may further comprise one or more reagents suitable for the detection of binding of the antibody to a target.

Also provided by the present invention are pharmaceutical compositions comprising WF6 antibody produced by cell line WF6, or an antibody having equivalent specificity thereto, or a functional equivalent thereof, and a pharmaceutically acceptable carrier.

BRIEF DESCRIPTION OF THE DRAWINGS

These and other aspects of the present invention will now be described by way of example only with reference to the accompanying drawings, in which:

FIG. 1 shows inhibition of WF6 antibody activity by various chondroitin sulfates;

FIG. 2 shows an absorbance profile of fractions of oligosaccharides containing chondroitin 6-sulfate from chondroitinase ABC digested CS-C eluted by column chromatography;

FIG. 3 shows the level of uronic acid in each fraction from FIG. 2 showing IC50 against WF6 antibody using competitive ELISA;

FIG. 4 shows the column profile of fraction 6 from FIG. 2 analysed by ion exchange FPLC;

FIG. 5 shows the effect of sulfatase digestion of the substrate on the reactivity of WF6 antibody;

FIG. 6 shows immunohistostaining of human skin tissue section using WFG as primary antibody;

FIG. 7 shows uronic acid content of cartilage from an animal model of cartilage degradation;

FIG. 8 shows levels of WF6 epitope in samples from the animal model over time;

FIG. 9 shows the level of WF6 epitope in serum of human patients with osteoarthritis and rheumatoid arthritis;

FIG. 10 shows the effect of chitosan polysulfate on levels of WF6 epitope on a dog model of cartilage degradation;

FIG. 11 shows levels of WF6 epitope in cartilage explants induced by retinoic acid; and FIG. 12 shows levels of proteoglycans containing WF6 epitope in serum from cancer patients.

DETAILED DESCRIPTION OF THE DRAWINGS

1. The Production of Hybridoma Cells which Produce an Antibody Against Chondroitin 6-Sulfate.

Purified proteoglycans (A1D1 fraction) from embryonic shark cartilage were used as antigen for the induction of an immune response in Balb/c mice. Spleen cells from mice which gave a high titer of antibody to chondroitin 6-sulfate (chondroitin sulfate C; CS-C) were fused with myeloma cell line X63 Ag8.653 in the ratio of 5:1. The fused cells were cultured in medium containing hypoxanthine, aminopterine, and thymine. Cell cultures were then tested for the production of antibodies by ELISA technique using chondroitin 6-sulfate (chondroitin sulfate C) as coating antigen. A positive cell line was isolated as a monoclone using a limiting dilution technique. The resulting cell line which produced antibody specifically against chondroitin 6-sulfate was called WF6, and it was found that the isotype of this antibody is Ig M, with Kappa-light chain. The cell line has been deposited with the American Type Culture Collection (ATCC) on 11 Aug. 2004, under accession number PTA-6157.

2. The Production of Monoclonal Antibody Against Chondroitin 6-Sulfate in Ascitic Fluid and Serum Free-Medium.

The mass production of this monoclonal antibody WF6 (MAb WF6) can be performed using hybridoma cells injected into the intraperitoneal cavity of Balb/c mice which have been primed by injection with 0.5 ml pristane one week before. Ascitic fluid samples can be obtained after 2-4 weeks which contain a large quantity of MAb WF6.

An alternative technique for mass production makes use of serum-free medium. The hybridoma cell WF6 can be cultured in 10% fetal calf serum Iscove's modified Eagle's medium, with gradual reduction of the percentage of serum to 5%, 1% and 0% along with an increase in commercial serum-free medium. The final medium should be 100% serum-free media which has been formulated with growth factors. The cells were cultured in 5% CO2, and 95% humidity and 37 degree C. The supernatant of this media may be further evaluated for antibody activity by ELISA technique and purified further using ammonium sulfate precipitation and chromatography.

3. Characterization of the Monoclonal Antibody WF6 by ELISA 3.1 Coat plate (polystyrene, Maxisorp Nunc®) with proteoglycans (fraction A1, aggregated from of shark cartilage proteoglycans) and block with 1% BSA 3.2 Prepare the inhibition mixture containing the optimal dilution of MAb WF6 and inhibitor, or standards or unknown samples in equal volume (175+175 µL each) in plastic tubes (1.5 mL tubes), then incubate at 37 degree C. for 1 hour.

3.3 Add the inhibition mixture from 3.2 to the coated and blocked plate at 100 µL/well, and triplicate per sample (three wells), then incubate at 37 degree C. for 1 hour.

3.4 Wash plate with washing buffer (PBS-Tween 0.05%) three times and dry before addition of 100 µL per well of peroxidase conjugated anti-Ig M antibody, then incubate at 37 degree C. for 1 hour.

3.5 Wash plate with washing buffer three times, and dry before adding OPD substrate (100 µL/well), incubate for 15 minutes in the dark, and then stop the reaction by adding of 4 M sulfuric acid (50 µL/well). Absorbance of the plate was then measured 492/690 nm by microplate reader.

3.6 The inhibition graph was plotted showing concentration of inhibitors (or standards) against absorbance (see FIG. 1). A range of test compounds were used, being chondroitin sulfate A to E, and the A1D1 proteoglycan fraction.

It was found that the monoclonal antibody shows reactivity (measured as inhibitory activities) only to chondroitin 6-sulfate (CS-C) and CS-D. It was later determined that the CS-D standard compounds contained some chondroitin 6-sulfate units, such that we believe the WF6 antibody shows specificity for chondroitin 6-sulfate containing compounds having a specific pattern of sulfation.

4. Specificity of Monoclonal Antibody WF6 against Oligosaccharides Containing Chondroitin 6-Sulfate.

4.1 Chondroitin 6-sulfate (CS-C) from commercial shark cartilage (Sigma-Aldrich Chemical) was digested with chondroitinase ABC which cleaved the CS-C into small oligosaccharides at various sites. The cleavage products have a double bond at the non-reducing end of the products which has maximal absorption at 232 nm.

4.2 The products from enzyme digestion were separated by column chromatography using a BioGel P-6 column. The absorbance of the column fractions was measured, giving the profile shown in FIG. 2.

4.3 The products can be divided into 10 fractions as shown in FIG. 2. Each fraction was pooled and concentrated by freeze drying, and the reactivity against MAb WF6 was determined using the method described in section 3. The reactivities from each fraction were compared by calculation of the uronic acid content which gave 50% inhibition (IC50; inhibition concentration at 50%), the results of which are shown in FIG. 3. Percentage inhibition can be calculated by % inhibition 100 [((A(sample)−A (blank))/(A(control)−A(blank))× 100)] where A=absorbance.

It was found that the oligosaccharide fractions which still displayed inhibitory activities were fractions 1-6, and by comparison to known standards from previous studies, we determined that fraction number 6 should contain oligosaccharides having 8-12 sugar units (octasaccharides-dodecasaccharides).

4.4 Fraction number 6 of the oligosaccharides was further purified using by ion-exchange chromatography using FPLC and Mono-Q column chromatography using lithium percholate as eluent. The obtained column profile is shown in FIG. 4.

From the experimental results above, it was found that the oligosaccharides from gel filtration consisted of various species of chondroitin 6-sulfate oligosaccharides. This demonstrates that the monoclonal antibody WF6 reacts with oligosaccharides containing chondroitin 6-sulfate that have a special pattern of sulfatation as shown in the fingerprinting of Mono-Q ion-exchange FPLC.

5. A Sulfate Group at Position 6 is Significant for Reaction Against Monoclonal Antibody WF6

5.1 The oligosaccharide fractions d, e and f from the column profile shown in FIG. 4 were subjected to digestion with 4- and 6-sulfatase.

5.2 The products from these two enzymes were further evaluated for reactivity against MAb WF6 using competitive ELISA technique as described in section 3.

5.3 The comparison of the reactivities in each product, including a pre-digested sample, is shown in FIG. 5. It was found that the sulfate group on the oligosaccharides is required for reactivity against MAb WF6.

CONCLUSION

When taken together, the results described in sections 3 to 5 above demonstrate that MAb WF6 has reactivity against oligosaccharides and polysaccharides of at least 8 sugar units containing chondroitin 6-sulfate. Furthermore, this reactivity of MAb WF6 requires the functional group of 6-sulfate at the terminal residue because the 6-sulfatase recognises this position. And 4-sulfate needs to be an accessory group, including the specific sulfating pattern along with the oligosaccharide chain.

6. The Use of Monoclonal Antibody WF6 in Immunohistostaining of Tissues 6.1 Skin tissue samples from the pathological laboratories which had been processed by routine procedures in tissue staining were selected for this study.

6.2 The optimal dilution of MAb WF6 in PBS (for example, 1:500 from ascitic fluid, and 1:100 tissue culture media) was used as primary antibody in the staining procedure after the tissue section was fixed to the slides.

6.3 Excess antibody was washed from the slide with washing buffer and re-stained with peroxidase conjugated anti-IgM antibody.

6.4 Excess conjugates and non-reacted antibody were washed from the slides, and insoluble substrate added.

6.5 The enzyme reaction was stopped with acid and excess colour washed out; the sample was then observed under light microscope as shown in FIG. 6.

7. The Application of Monoclonal Antibody WF6 for the Evaluation of Cartilage Degradation in an Animal Model 7.1 The animal model was run as previously reported (Kongtawelert et al, 1989) for the induction of cartilage degradation by intra-articular injection of hydrocortisone (Solu-Cortef®). The rabbits were divided into two groups: the control had normal saline solution injection, while the experimental group had hydrocortisone injection of 200 mg in every week for up to 12 weeks. Each week before injection the animal was bled for serum preparation.

7.2 The serum samples from each week were assayed for the level of WF6 epitope using the method described in section 3. In addition to this study, the MAb 3B3 (Caterson et al, 1990) has also been used as a biosynthesis marker in cartilage as previously reported.

7.3 At the end of the study, all animals were sacrificed and the articular cartilage were collected for analysis of proteoglycan contents as uronic acid per dried weight of cartilage. This data is shown in FIG. 7.

7.5 The level of the WF6 epitope and 3B3 epitope in each week were used to calculate the percentage relative change of each epitope each week. The results are shown in the graph of FIG. 8.

It was found that the monoclonal antibody WF6 can be used or applied to use in the technique of immunoassay (competitive ELISA) for quantitation of proteoglycans containing the chondroitin 6-sulfate epitope, and this assay indicates that it can be used as a marker for degradation of cartilage. FIG. 8 shows that the WF6 epitope was found at significantly higher levels in hydrocortisone treated animals than normal saline treated animals, and the Figure also demonstrates the early indication of disease activity.

8. The Application of MAb WF6 for Quantitation of Biomarker in Diagnosis of Osteoarthritis (OA) and Rheumatoid Arthritis (RA)

8.1 Human serum samples from patients with OA, RA and healthy patients were collected to analyze the WF6 epitope. The samples were diluted 5 folds with 6% BSA-PBS to reduce non-specific binding.

8.2 All serum samples were subjected to analysis using competitive ELISA as described in section 3 using shark proteoglycan fraction A1 as relative standards.

8.3 The age of volunteers in each group was not significantly different.

8.4 The level of WF6 epitope from individual samples were plotted as a scatter graph as shown in FIG. 9.

It was found that the MAb WF6 can be applied to use in a quantitative assay using immunological method for diagnosis of OA, and RA. However, there were still overlapping of the value in some samples of each group, which might be from the variation of the disease stage, and the treatment of the individual person. In addition, this might be interpreted as showing that the level of WF6 epitope can be used to monitor the disease activities and prognosis as well.

9. The Application of Monoclonal Antibody WF6 for Monitoring of Treatment in an Animal Model 9.1 Cruciate ligament transection is used to induce the degradation of cartilage (OA) in 6 dogs by surgical operation at the hind leg (see Batiste et al, 2004).

9.2 These dogs were divided into 2 group (3 each group), one group were injected intramuscularly with normal saline solution and the other group injected with chitosan polysulfate, which is a potential anti-osteoarthritis agent, at the dose of 3 mg/kg body weight. The injection was given every week for eight weeks.

9.3 The third group of dogs was not surgically operated upon, and was injected with chitosan polysulfate intramuscularly at 3 mg/kg body weight.

9.4 All of the animals were observed and cared for by a veterinarian. Blood for serum preparation was collected to use for the determination of WF6 by the method described in section 3.

9.5 The relative changes of all experimental animals were averaged in each group and the graph was plotted against time of the study as shown in FIG. 10.

It was found that the MAb WF6 can be used in the method of quantitation of its epitope in animal model and can be applied as a marker for monitoring the treatment of the disease, like cartilage degeneration.

10. The Application of Monoclonal Antibody WF6 in the Monitoring of Cartilage Degradation in Tissue Culture Model of Cartilage Explants 10.1 Porcine cartilage was sterile cut into small pieces and cultured in serum-free media under 37 degree C., and 5% carbon dioxide.

10.2 Retinoic acid was added to the culture at the concentration of 10 uM for stimulation of cartilage degradation.

10.3 The media were collected every other day for four weeks for determining the level of WF6 epitope using the method described in section 3.

10.4 The level of WF6 epitope from each week was plotted against time (days) of culture as shown in FIG. 1.

It was found that the MAb WF6 can be used for monitoring the degradation of cartilage if vitro by a well established technique using the induction of retinoic acid when compared with the control. This demonstration showed the applicability of MAb WF6 as a research tool for the cartilage degradation in vitro.

11. The Application of the Monoclonal Antibody WF6 for the Quantitation of a Biomarker in Ovarian Cancer Serum Samples From previous reports (Nash et al, 2002), it was found that there were increased levels of chondroitin sulfate biosynthesis in cancer tissues compared with normal tissues. Furthermore, the cancer cells can produce some kinds of enzymes that can degrade the connective tissues surrounding them. These would make cancer cells intrude through the tissue and metastasize to other areas. We therefore suggest that MAb WF6 could be used for diagnosis of this pathogenesis including the tumour tissues.

11.1 Serum samples were collected from normal patients, patients having a tumour (non-cancer), and patients with ovarian cancers. This study was approved by the Ethics Committee.

11.2 All serum samples were tested for the determination of WF6 epitope level and compared between group of normal, non-cancer (tumour) and cancer. The results are shown in FIG. 12

It was found that the WF6 epitope can be used as a biomarker for the cancerous (ovarian) condition in human.

REFERENCES

1. Howell D S. Pathogenesis of osteoarthritis. Am J Med 1986; 80(4B):24-8

2. Muir H. and Hardingham T E. "Structure of proteoglycan" Biochemistry of carbohydrate. W. J. Ehelan Ed. 1975; 5:153
3. Hochberg M c., Altman R D., Brandt K D., Clark B M., Dieppe P A., Griffin M R., Moskowitz R W., Schnitzer T J. Buidselines for the medical management of osteoarthritis. Part II. Ostroarthritis of the knee. American Collage of Rheumatology. Arthritis Rheum 1995; 38(11); 1541-6
4. Fassbender H G. Joint destruction in various arthritic disease. Articular cartilage biochemistry 1986: 371-90
5. Sexne T. and Heinegard D. Involvement of nonarticular cartilage, as demonstrated by release of cartilage specific protein in Rheumatoid arthritis. Arthritis Rheum; 32(9): 1080-86.
6. Hardingham T. and Bayliss M. Proteoglycans of articular cartilage: Change in aging and in joint disease. Seminar in arthritis and rheumatism. 1990; 20(3); 12-33
7. Caterson B., Christner J E., Baker T R. Characterization of monoclonal antibody that specifically recognizes corneal and skeletal keratan sulphate. J Biol Chen 1983; 258: 8848-54
8. Caterson B., Christner J E., Baker J R. Monoclonal antibodies against chondroitin sulphate isomer: their use as probes for investigating proteoglycan metabolism. Biochem Soc Trans. 18, 820-3
9. Nathachai T. (1996) Production and characterization of monoclonal antibody against chondroitin 6-sulfate. M.S. Thesis, Chiang Mai University, 1997
10. Damrasamon S. (1997) The development of methods for quantitation of serum total sialic acid and hyaluronan. M.S. Thesis, Chiang Mai University, 1998
11. Heinegard D., Hascall V C. Aggregation of cartilage proteoglycan III. Characterizations of the proteins isolated from trysin digests of aggregate. J Biol Chem 1974; 249 (13): 4250-6
12. Fraser J R., Appelgren L E., Laurent T C. Tissue uptake of circulating hyarulonic acid: A Whole body autoradiographic study. Cell Tissue Res 1983; 233:285-93
13. Ratcliffe A., Shurety W., Caterson B. The quantitation of a native chondroitin sulphate epitope in synovial fluid lavages and articular cartilage from canine experimental osteoarthritis and disuse atropy. Arthritis Rhem 1993; 36(4): 543-51
14. Kempson G E., Tuke M A., Dingle J T., Barrett A J., Horsfield P H. The effects of proteolytic enzymes on the mechanical properties of adult human articular cartilage. Biochim Biophys Acta 1976; 428(3); 741-60
15. Ratcliffe A. and Seibel M J. Biochemical markers of osteoarthritis. Curr Opin Rheumatol 1990; 2: 770-6
16. Caterson B., Baker J R., Christner J E. Immunological methods for the detection and determination of connective tissue proteoglycan. J Invest Dermatol 1982; 79(suppl 1): 45s-50s
17. Williams J M., Downey C., Thonar E J., Increase in level of serum keratan sulfate following cartilage proteoglycan degradation in the rabbit knee joint. Arthritis Rheum 1988; 31(5): 557-60
18. Sweet M B., Coelho A., Schnitzer C M., Schnitzer T J., Lenz M E., Jakim I., Kuetlner K E., Thonar E J. Serum keratan sulfate levels in osteoarthritis patients. Arthritis Rheum 1988; 31(5): 648-52
19. Spector T D., Woodward L., Hall G M., Hammond A., Williams A., Butler M G., James I T., Hart D J., Thompson P W., Scott D L. Keratan sulfate in rheumatoid arthritis, osteoarthritis ans inflammatory disease. Ann Rheum Dis 1992; 51(10): 1134-7
20. Ghosh P., Sutherland J M., Taylor T K., Bellenger C R., Pettit G D. The effect of bilateral medial meniscectomy on articular cartilage of the hip joint. J Rheumatol 1984; 11(2): 197-201
21. Sharif M., George B., Shepstone L., Knudson W., Thonar E J-M A., Cushnaghan S., Dieppe P. Serum hyaluronic acid level as a predictor of disease progression in osteoarthritis of the knee. Arthritis Rheum 1995; 38: 760-7
22. Cooper E H. And Rathbone B J. Clinical significance of the immunometric measurements of hyaluronic acid. Ann Clin Biochem 1990; 27: 444-51
23. Smith P K., Krohn R I., Hermanson G T., Mallic A K., Garther F H., Prorenzano M D., Fujimoto B K., Goeke N M., Olson B J. and Klenk D C. Measurement of protein using by bicinchoninic acid. Anal Biochem 1985; 150(1): 76-85
24. Farndale R H. And Buttle D J. Improved quantitative and discrimination of sulfated glycosaminoglycans by use of dimyethylene blue. Biochemica-Biophysica Acta 1986; 883: 173-77
25. Blumenlcrantz N. and Asboe-Hansen G. New method for quantitative determination of uronic acids. Anal Biochem 1973; 54:484-89
26. Kongtawelert P, Brooks P M, Ghosh P. Pentosan polysulfate (Cartrophen) prevents the hydrocortisone induced loss of hyaluronic acid and proteoglycans from cartilage of rabbit joints as well as normalizes the keratan sulfate levels in their serum. J. Rheumatol. 1989 November; 16(11): 1454-9.
27. Caterson B, Mahmoodian F, Sonrell J M, Hardingsham T E, Bayliss M T, Carney S L, Ratcliffe A, Muir H. Modulation of native chondroitin sulphate structure in tissue development and in disease. J Cell Sci. 1990 November; 97 (Pt 3):411-7.
28. Batiste D L, Kirkley A, Laverty S, Thain L M, Spouge A R, Gati J S, Foster P J, Holdswortlh D W. High-resolution MRI and micro-CT in an ex vivo rabbit anterior cruciate ligament transection model of osteoarthritis. Osteoarthritis Cartilage. 2004 August; 12(8):614-26.
29. Nash M A, Deavers M T, Freedman R S. The expression of decorin in human ovarian tumors. Clin Cancer Res. 2002 June; 8(6): 1754-60.]

The invention claimed is:
1. A method of producing monoclonal antibodies, the method comprising:
culturing hybridoma cells as deposited with ATCC under accession number PTA-6157 in a suitable growth medium under conditions suitable for producing monoclonal antibodies; and
harvesting growth supernatant of the growth medium to obtain the monoclonal antibodies,
wherein the monoclonal antibodies exhibit reactivity only to an epitope of an oligosaccharide or polysaccharide chondroitin sulfate, said chondroitin sulfate epitope containing at least 8 sugar units and having each of a terminal chondroitin 6-sulfate unit and a chondroitin 4-sulfate accessory unit.

* * * * *